(12) United States Patent
Orlando et al.

(10) Patent No.: US 11,712,530 B1
(45) Date of Patent: Aug. 1, 2023

(54) NON-INVASIVE RESPIRATORY DEVICE WITH A VERTICAL CONNECTION INTERFACE

(71) Applicant: Nanotronics Health, LLC., Brooklyn, NY (US)

(72) Inventors: Julie A. Orlando, Copley, OH (US); Stephen E. Delaporte, Brooklyn, NY (US); John B. Putman, Celebration, FL (US)

(73) Assignee: Nanotronics Health, LLC., Brooklyn, NY (US)

( * ) Notice: Subject to any disclaimer, the term of this patent is extended or adjusted under 35 U.S.C. 154(b) by 0 days.

(21) Appl. No.: 17/934,775

(22) Filed: Sep. 23, 2022

(51) Int. Cl.
| | |
|---|---|
| *A61M 16/00* | (2006.01) |
| *A61M 16/16* | (2006.01) |
| *A61M 16/10* | (2006.01) |
| *A61L 2/10* | (2006.01) |
| *A61M 16/20* | (2006.01) |

(52) U.S. Cl.
CPC ...... *A61M 16/0069* (2014.02); *A61M 16/109* (2014.02); *A61M 16/16* (2013.01); *A61L 2/10* (2013.01); *A61M 16/024* (2017.08); *A61M 16/209* (2014.02); *A61M 2016/0027* (2013.01); *A61M 2205/3331* (2013.01); *A61M 2205/3368* (2013.01)

(58) Field of Classification Search
CPC .......... A61M 16/0057; A61M 16/0066; A61M 16/0069; A61M 16/024; A61M 16/109; A61M 16/16; A61M 16/209; A61M 2016/0027; A61M 2205/3331; A61M 2205/3368

See application file for complete search history.

(56) References Cited

U.S. PATENT DOCUMENTS

| | | | | |
|---|---|---|---|---|
| 4,941,469 | A * | 7/1990 | Adahan | A61M 16/0833 128/205.24 |
| 2006/0191531 | A1* | 8/2006 | Mayer | A61M 16/0816 128/200.11 |
| 2008/0072900 | A1* | 3/2008 | Kenyon | A61M 16/024 128/204.18 |
| 2008/0099017 | A1* | 5/2008 | Bordewick | A61M 16/0057 128/204.21 |
| 2010/0132708 | A1* | 6/2010 | Martin | A61M 16/0816 128/204.21 |

(Continued)

*Primary Examiner* — Joseph D. Boecker
(74) *Attorney, Agent, or Firm* — DLA Piper LLP (US)

(57) ABSTRACT

A positive airway pressure device includes a primary housing and a humidification system. The primary housing includes an outer edge, a first electronic connection portion, and a blower configured to deliver a vapor to a patient. The humidification system includes a water reservoir configured to hold a liquid, a heating plate in thermal communication with the water reservoir, a second electronic connection portion, and a lid configured to selectively shield the second electronic connection portion. The primary housing is configurable between at least two positions relative to the humidification system. The at least two positions include a first position in which the lid at least partially shields the second electronic connection portion and a second position in which the outer edge of the primary housing forces open the lid such that the first electronic connection portion mates with the second electronic connection portion.

14 Claims, 9 Drawing Sheets

(56) References Cited

U.S. PATENT DOCUMENTS

| | | | | |
|---|---|---|---|---|
| 2011/0023874 | A1* | 2/2011 | Bath | A61M 16/06 |
| | | | | 128/203.14 |
| 2011/0155132 | A1* | 6/2011 | Virr | A61M 16/1075 |
| | | | | 128/203.26 |
| 2011/0253136 | A1* | 10/2011 | Sweeney | A61M 16/161 |
| | | | | 128/207.18 |
| 2012/0146251 | A1* | 6/2012 | Heine | A61M 16/1075 |
| | | | | 261/119.1 |
| 2020/0368468 | A1* | 11/2020 | Liu | A61M 16/109 |
| 2020/0368484 | A1* | 11/2020 | Zhi | A61M 16/16 |
| 2021/0093825 | A1* | 4/2021 | Lin | A61M 16/0816 |
| 2021/0128866 | A1* | 5/2021 | Higashiyama | A61M 16/145 |
| 2022/0016377 | A1* | 1/2022 | Maeda | A61M 16/024 |
| 2022/0016383 | A1* | 1/2022 | Workman | A61M 16/022 |
| 2022/0379068 | A1* | 12/2022 | Walls | A61M 16/20 |
| 2022/0409844 | A1* | 12/2022 | Hungr | A61M 16/0875 |

* cited by examiner

FIG. 8B

NON-INVASIVE RESPIRATORY DEVICE WITH A VERTICAL CONNECTION INTERFACE

FIELD OF DISCLOSURE

The present invention relates generally to non-invasive ventilators and more particularly to continuous positive air pressure and bi-level positive air pressure devices.

BACKGROUND

Non-invasive ventilation (NIV) is often used for patients experiencing respiratory distress. This may be prescribed for patients with Obstructive Sleep Apnea (OSA), Chronic Obstructive Pulmonary Disorder (COPD), pneumonia, or other respiratory disorders. NIV is often prescribed through a respiratory device that supplies positive air pressure (PAP) to the patient with a face mask or other patient interface such as a nasal pillow. Depending on the disorder and clinical treatment protocol, the PAP may be either continuous positive air pressure (CPAP) or bi-level positive air pressure (Bi-level PAP).

SUMMARY

In some embodiments, a positive airway pressure device is disclosed herein. The positive airway pressure device includes a primary housing and a humidification system. The primary housing includes an outer edge, a first electronic connection portion, and a blower configured to deliver a vapor to a patient. The humidification system includes a water reservoir configured to hold a liquid, a heating plate in thermal communication with the water reservoir, a second electronic connection portion, and a lid configured to selectively shield the second electronic connection portion. The primary housing is configurable between at least two positions relative to the humidification system. The at least two positions include a first position in which the lid at least partially shields the second electronic connection portion and a second position in which the outer edge of the primary housing forces open the lid such that the first electronic connection portion mates with the second electronic connection portion.

In some embodiments, a positive airway pressure device is disclosed herein. The positive airway pressure device includes a primary housing, a humidification system, and a controller. The primary housing includes a first electronic connection portion, and a blower configured to deliver a vapor to a patient. The humidification system includes a water reservoir configured to hold a liquid, a heating plate in thermal communication with the water reservoir, and a second electronic connection portion configured to interface with the first electronic connection portion. The controller is in communication with the blower and at least one of the first electronic connection portion or the second electronic connection portion.

In some embodiments, a positive airway pressure device is disclosed herein. The positive airway pressure device includes a primary housing, a humidification system, and a controller. The primary housing includes a first electronic connection portion, a blower configured to deliver a vapor to a patient, a first sensor at least partially disposed in a gas pathway, the first sensor configured to measure a pressure of the positive airway pressure device, and a second sensor at least partially disposed in the gas pathway, the second sensor configured to measure a temperature in the positive airway pressure device. The humidification system includes a water reservoir configured to hold a liquid, a heating plate configured to heat the liquid in the water reservoir, and a second electronic connection portion configured to interface with the first electronic connection portion. The controller is in communication with the blower and at least one of the first electronic connection portion or the second electronic connection portion. The controller configured to perform operations. The operations include initializing the blower of the positive airway pressure device to deliver an initial therapy pressure to the patient. The operations further include initializing the heating plate to deliver a therapy pressure to the patient. The operations further include receiving, by the controller from the first sensor or the second sensor, real-time respiratory response data while delivering therapy to the patient. The operations further include determining that a sleep disruption has occurred based on the real-time respiratory response data. The operations further include, based on the determining, initiating an action to account for the sleep disruption.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrated only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

During respiratory PAP ventilation, many patients typically experience discomfort from the relatively dry air supplied by the respiratory device. In such circumstances, it is often helpful to humidify the pressurized air before the air is supplied to the patient. This humidification may be mechanically and electrically integrated into the respiratory device to allow for a streamlined supply of pressurized air to the patient.

One or more techniques described herein provides an integrated humidification system for respiratory devices, such as a PAP device, by allowing a humidifier of the PAP device to be vertically connected mechanically and electrically to the PAP device, automatically protecting the electrical connection interface of the heating subsystem, and automatically sealing the humidifier chamber.

Figure 1:
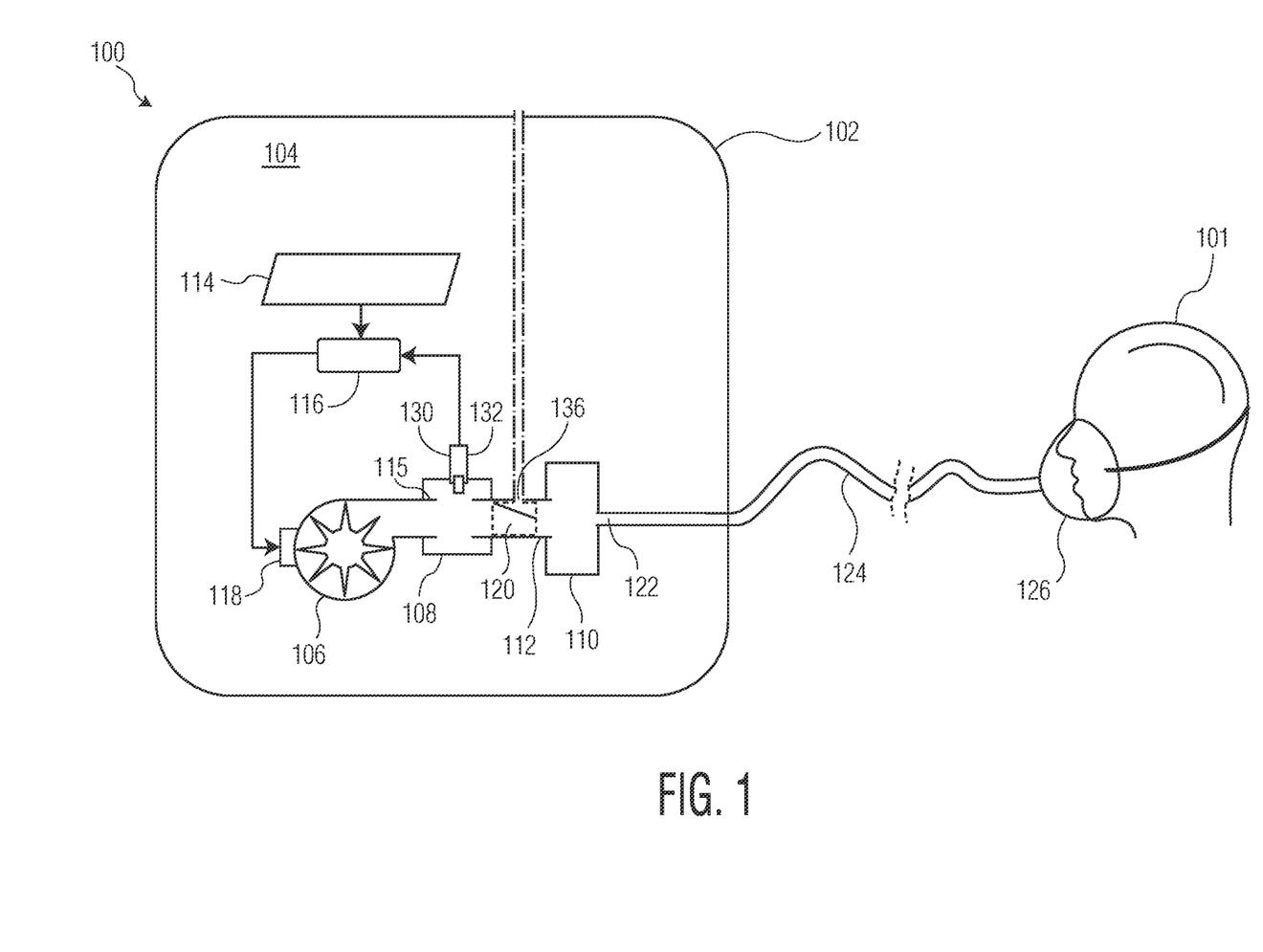
FIG. 1 is a block diagram illustrating a positive airway pressure (PAP) device with interface to a patient, according to example embodiments.

FIG. 1 is a block diagram illustrating a positive airway pressure (PAP) device 100 with interface to a patient 101, according to example embodiments. As shown, PAP device 100 may include a body 102 defining an interior volume 104. PAP device 100 may include a blower 106, a gas manifold 108, a buffer chamber 110, a connector 112, a humidification system 115, and a microprocessor 114 disposed in interior volume 104.

Blower 106 may be configured to deliver air to gas manifold 108. Blower 106 may include a blower controller 116 associated therewith. Blower controller 116 may be configured to control operation of blower 106. For example, blower controller 116 may be configured to provide electrical input to blower 106 to control a speed of blower 106. For example, blower controller 116 may provide blower 106 with electrical input to obtain a setpoint pressure. In some embodiments, blower controller 116 may provide electrical input to blower terminal block 118 to control speed of blower 106. The speed of blower 106 may be directly related to the maintained pressure.

Gas manifold 108 may be configured to fluidly couple blower 106 with buffer chamber 110. Buffer chamber 110 may be configured to maintain a volume of gas that is removed from blower 106. For example, gas may flow from blower 106, through gas manifold 108, and into buffer chamber 110.

Connector 112 may be configured to couple buffer chamber 110 with gas manifold 108. Connector 112 may provide a flow channel from gas manifold 108 to buffer chamber 110. As shown, in some embodiments, connector 112 may include check valve 120. Check valve 120 may be representative of a one-way valve or gate configured to prevent backflow of gas into blower 106. For example, check valve 120 may be configured to prevent gas at higher pressure from flowing back into blower 106 from buffer chamber 110. If, for example, blower 106 is turned off, check valve 120 may be configured to prevent air from escaping back through blower 106. Such prevention may result in a more consistent control of the delivered pressure and may reduce influence from a patient's respiratory response. In some embodiments, check valve 120 may be designed such that, when blower 106 is turned off, check valve 120 may open a path to external air. For example, check valve 120 may open a path to external air via check valve vent 136, thus allowing for any backflow pressure or gas to be exhausted from PAP device 100. Vent 136 may be located proximate the exterior of PAP device 100. Such functionality may ensure that the patient is not asphyxiated in the case of a power failure.

Although PAP device 100 is illustrated as including a gas manifold 108 and a buffer chamber 110, in some embodiments, PAP device 100 may simply include a single unit acting as both gas manifold 108 and buffer chamber 110.

As shown, PAP device 100 may further include a patient connection port 122. Patient connection port 122 may be configured to output gas to a patient delivery system 124. For example, patient connection port 122 may be representative of a port in communication with buffer chamber 110. In operation, patient delivery system 124 may be detachably coupled to PAP device 100. Patient delivery system 124 may be representative of tubing that delivers gas to patient 101 via patient interface 126 (e.g., mask).

PAP device 100 may further include a sensor 130 and a sensor 132. Sensor 130 and/or sensor 132 may be positioned in a gas pathway of PAP device 100. For example, a gas pathway may refer to the flow channel encompassing all areas where the air flows from the air intake through to patient connection port 122. In some embodiments, such as that shown, sensor 130 and/or sensor 132 may be at least partially disposed in gas manifold 108. In some embodiments, sensor 130 and/or sensor 132 may be at least partially disposed in blower 106. Generally, sensor 130 and/or sensor 132 may be disposed anywhere within PAP device 100 such that it is in close proximity to blower 106. Sensor 130 may be configured to monitor pressure and provide feedback to blower controller 116 such that blower controller 116 can maintain a set pressure. For example, sensor 130 may send to blower controller 116 a control signal that represents a measured pressured in gas manifold 108. If the setpoint pressure differs from the control signal pressure, blower controller 116 may increase or decrease the speed of blower 106 to maintain the setpoint pressure. In this manner, blower controller 116 may work in conjunction with sensor 130 to provide a feedback loop for maintaining a desired level of pressure.

Sensor 132 may be configured to monitor temperature and provide feedback to microprocessor 114. For example, sensor 132 may send to microprocessor 114 a control signal that represents a measured temperature in gas manifold 108. If the setpoint temperature differs from the control signal temperature, microprocessor 114 may increase or decrease the temperature.

Although not explicitly shown, those skilled in the art understand that more than one sensor may be implemented in the following processes. For example, U.S. application Ser. No. 17/659,971, which is incorporated by reference herein in its entirety, describes a two sensor PAP device that may implement the present processes. In such embodiments, a first sensor may be used for training while the second sensor may be used for control.

Humidification system 115 may be configured to humidify the pressurized air delivered to patient 101. For example, humidification system 115 may be located within a gas pathway of PAP device 100. Humidification system 115 may include a humidifier. The humidifier may be configured to hold liquid for delivering vapor to patient 101 during use of PAP device 100. A more detailed discussion of humidification systems for use with PAP device 100 may be found in more detail below.

In some embodiments, humidification system 115 may include an ultraviolet light. The ultraviolet light may be used to sterilize the water in humidification system 115. In this manner, the ultraviolet light can ensure that the vapor delivered to the user is free from contaminants.

Microprocessor 114 may be configured to control operation of PAP device 100. For example, microprocessor 114 may be configured to control the pressure setpoint of blower 106. In some embodiments, the initial set point of blower 106 may be referred to as the therapy pressure. The therapy pressure may be set by the user or automatically determined by microprocessor 114. The therapy pressure may be delivered to patient 101 when patient 101 inspires. In some embodiments, the pressure delivered to patient 101 may be adjusted, based on various triggers.

Figures 2A, 2B, 2C:
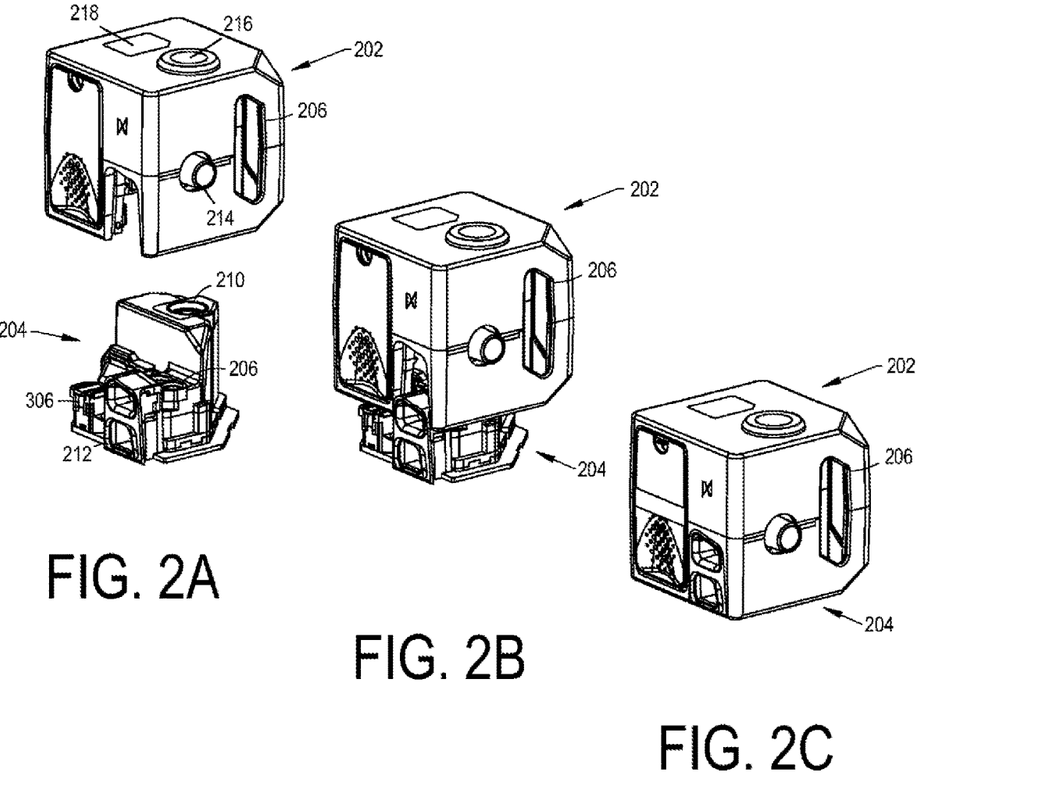
FIG. 2A is a perspective view of a PAP device in a first position, according to example embodiments.
FIG. 2B is a perspective view of the PAP device of FIG. 2A in a second position, according to example embodiments.
FIG. 2C is a perspective view of the PAP device of FIG. 2A in a third position, according to example embodiments.

FIGS. 2A-2C are perspective views of PAP device 100, according to example embodiments. FIG. 2A is a perspective view of PAP device 100 showing primary housing 202 detached from humidification system 204.

As shown, primary housing 202 may be configured to interface with humidification system 204. For example, primary housing 202 may be configured to interface with humidification system 204, such that humidification system 204 may be disposed substantially within an interior volume of primary housing 202 when in place. Generally, primary housing 202 and humidification system 204 may be arranged in a vertical coupling sequence through three positions, illustrated across FIGS. 2A-2C.

In the first position, such as that illustrated in FIG. 2A, primary housing 202 may be disconnected and hovering above humidification system 204. Primary housing 202 may include a handle 206. Handle 206 may be used by patient 101 or a user to vertically lower primary housing 202 over humidification system 204 or vertically remove primary housing 202 from humidification system 204.

FIG. 2B is a perspective view of PAP device 100 showing primary housing 202 and humidification system 204 in a second position. In the second position, primary housing 202 is shown being vertically dropped over humidification system 204.

FIG. 2C is a perspective view of PAP device 100 showing primary housing 202 and humidification system 204 in a third position. In the third position, primary housing 202 and humidification system 204 are shown fully connected.

As shown across FIGS. 2A-2C, PAP device 100 may include a latch mechanism 212. Latch mechanism 212 may be integrated with humidification system 204. Latch mechanism 212 may be configured to allow primary housing 202 and humidification system 204 to be securely connected with each other. Latch mechanism 212 may include a release switch interface that integrates a primary push button and an opening below the push button. The release switch may allow a user of the device (e.g., patient 101, clinician) to pinch the side of latch mechanism 212 with their index finger to force the push button inward with their thumb. Such latch mechanism 212 may allow the user of PAP device 100 to have more mechanical leverage when releasing primary housing 202 from humidification system 204.

As shown, in some embodiments, primary housing 202 may include patent connection port 214, a selection device 216, and a display 218. Patient connection port 214 may be configured to output gas to a patient delivery system (not shown). Selection device 216 may allow a user to dial in or select set points of the blower and/or the temperature of humidification system 204. In some embodiments, selection device 216 may be used to view usage statistics (e.g., hour of use) for PAP device 100. In some embodiments, selection device 216 may be representative of an encoder or encoder wheel. Display 218 may be configured to display operating information associated with PAP device 100 to end user. For example, via display 218, a user can see the set points of the blower, temperature of humidification system 204, metrics associated with PAP device 100, and the like.

Figures 3A, 3B:
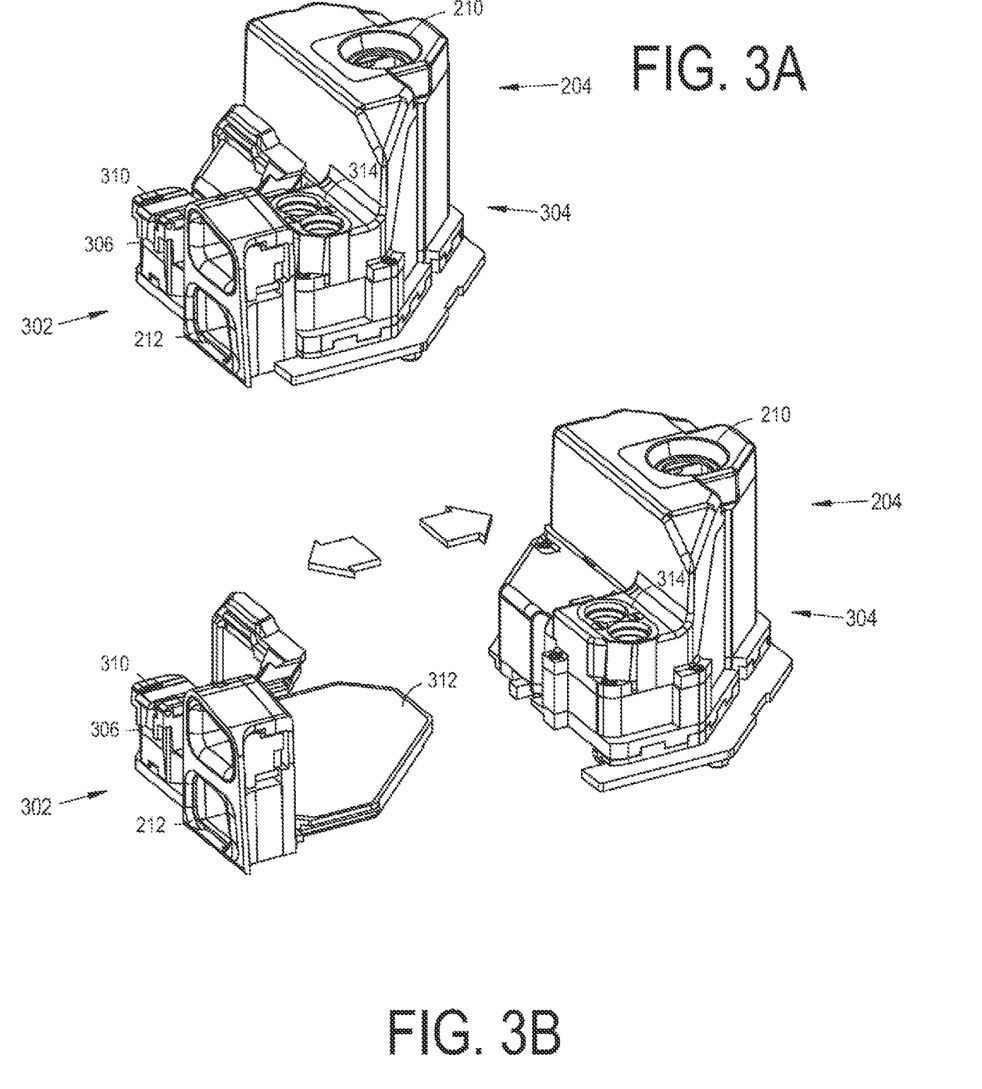
FIG. 3A illustrates a humidification system of a PAP device, according to example embodiments.
FIG. 3B is an exploded view of the humidification system of the PAP device of FIG. 3A, according to example embodiments.
Figure 3C:
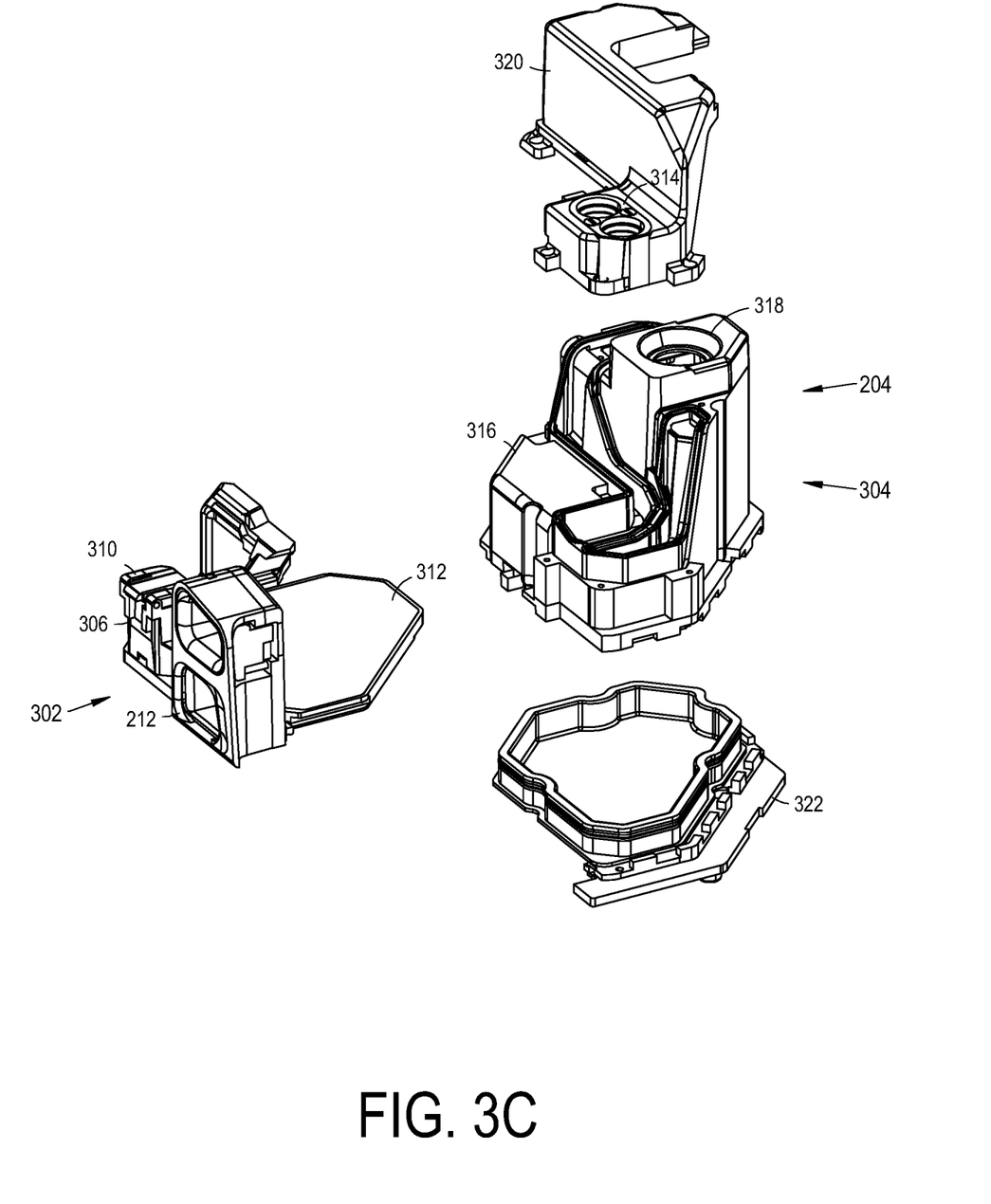
FIG. 3C is an exploded view of the humidification system of the PAP device of FIG. 3A, according to example embodiments.

FIG. 3A illustrates humidification system 204 of PAP device 100, according to example embodiments. FIG. 3B is an exploded view of humidification system 204 of PAP device 100, according to example embodiments. FIG. 3C is an exploded view of humidification system 204 of PAP device 100, according to example embodiments. For ease of discussion, FIGS. 3A, 3B, and 3C may be discussed and described together.

As shown, humidification system 204 may include heater module 302 and water chamber module 304. As shown, heater module 302 may be selectively coupled with water chamber module 304. For example, as shown in FIG. 3B, heater module 302 may slide into and out of position with water chamber module 304.

Heater module 302 may be configured to heat the water contained in heater module 302. Heater module 302 may include at least electronic connector interface 306, latch mechanism 212, lid 310, and heating plate 312. Electronic connector interface 306 may be representative of the electronic connections of PAP device 100, which may be configured to provide power to heating plate 312. In some embodiments, electronic connector interface 306 may further be configured to provide power to other electronic connections of PAP device 100, such as, but not limited to a signal connection for a thermistor.

Lid 310 may be configured to cover or protect electronic connector interface 306. For example, lid 310 may be configured to ensure that water and other debris do not enter electronic connector interface 306. In some embodiments, lid 310 may be representative of a spring-loaded lid that may be automatically lifted and opened when primary housing 202 is coupled with humidification system 204.

Heating plate 312 may be configured to heat the liquid in water chamber module 304. As shown, heating plate 312 may be configured to interface water chamber module 304. In some embodiments, power to heating plate 312 may be either constant currant, voltage, or pulse width modulation. In some embodiments, power levels of heating plate 312 may be set to maintain a temperature and humidity level that may be satisfactory for therapy.

Water chamber module 304 may include gas pathway connection interface 314, reservoir 316, and pour hole interface 318. Gas pathway connection interface 314 may be configured to directs air from the blower to humidification system 204 and to direct air out of humidification system 204 so that it can pass through patient outlet port 214.

Reservoir 316 may be configured to hold a liquid (e.g., water). In some embodiments, reservoir 316 may be filled using pour hole interface 318.

In some embodiments, water chamber module 304 may further include flow manifold 320. Flow manifold 320 may be configured to sit on top of water reservoir 316. For example, flow manifold 320 may be configured to provide a sealed gas pathway for allowing the air to flow into and out of water reservoir 316. Humidification of water may occur through hitting of heating plate 312, which may be configured to sit at the base of water reservoir 316 when heater module 302 is coupled with water chamber module 304.

In some embodiments, water chamber module 304 may further include a base plate 322. Base plate 322 may be configured to sit at bottom of water reservoir 316. For example, base plate 322 may be configured to retain heating plate 312. Base plate 322 may be configured as a track guide so that water chamber module 304 can slide into and snap together with heater module 302.

Figure 4A:
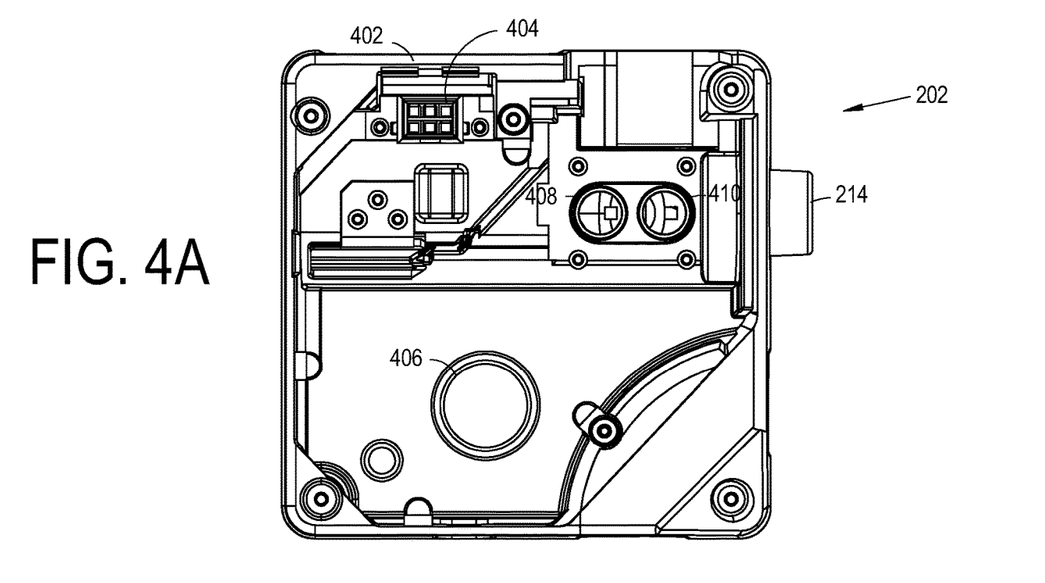
FIG. 4A illustrates a bottom view of a primary housing of a PAP device, according to example embodiments.
Figure 4B:
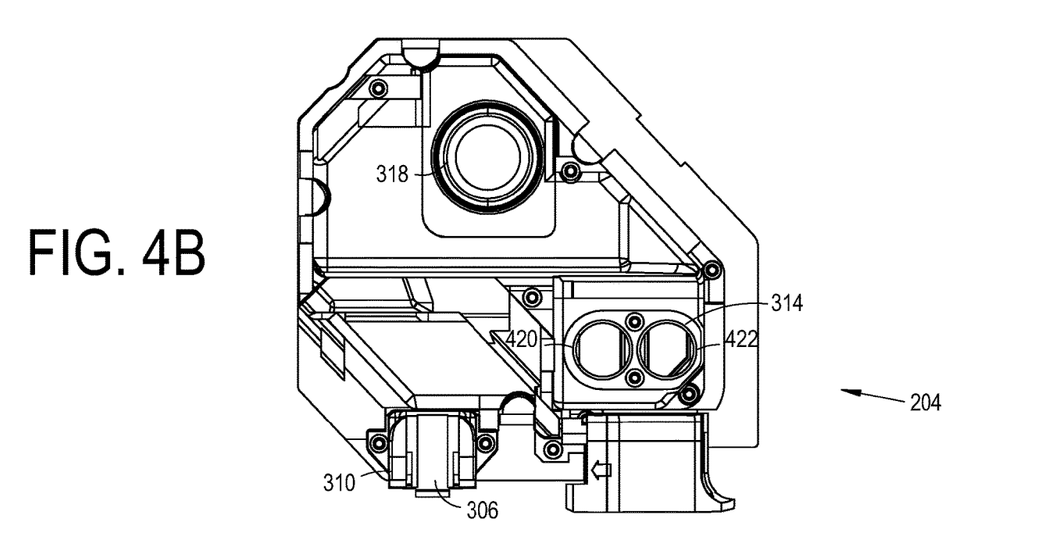
FIG. 4B illustrates a top-down view of a humidification system of the PAP device of FIG. 4A, according to example embodiments.

FIG. 4A illustrates a bottom view of primary housing 202, according to example embodiments. FIG. 4B illustrates a top-down view of humidification system 204, according to example embodiments. For ease of discussion, FIG. 4A may be discussed in conjunction with FIG. 4B.

As shown, primary housing 202 may include edge wall 402, male electronic connection interface 404, conical hub 406, and gas pathway ports 408, 410. Similarly, humidification system 204 may include gas pathway connection interface 314, electronic connector interface 306, and lid 310. Gas pathway connection interface 314 may include a humidifier inlet port 420 and a humidifier outlet port 422.

Gas pathway port 408 may be configured to direct the air from the blower to humidification system 204, when humidification system 204 is connected to humidifier inlet port 420. Gas pathway port 410 may be configured to direct the air out of humidification system 204, such that the air can pass through the patient outlet port 214, when gas pathway port 410 is connected to humidifier outlet port 422.

Conical hub 406 may be configured to extend from the primary housing 202 to automatically seal pour hole interface 318. For example, conical hub 406 may seal pour hole interface 318 through compression, as primary housing 202 and humidification system 204 may be coupled together.

As discussed above, lid 310 may be configured to cover or protect electronic connector interface 306. In some embodiments, lid 310 may be representative of a spring-loaded lid that may be automatically lifted and opened when primary housing 202 is coupled with humidification system 204. Such functionality may be possible because edge wall 402 may be configured to force lid 310 open as primary housing 202 is vertically lowered over humidification system 204.

Figure 5A:
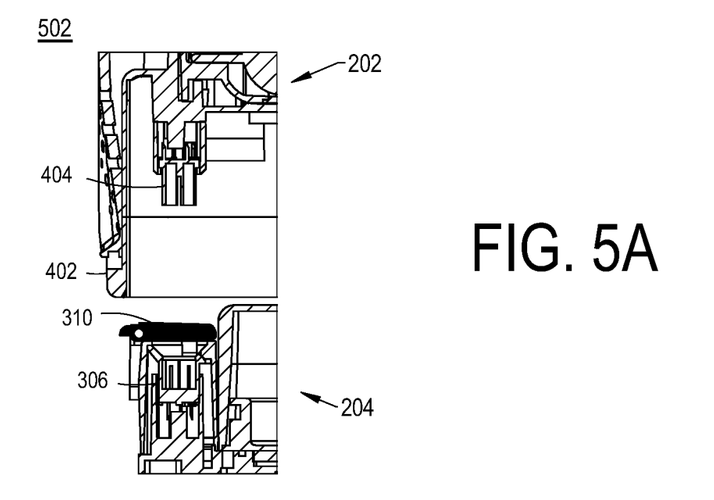
FIG. 5A is a sectional view illustrating PAP device in a first position, according to example embodiments.
Figure 5B:
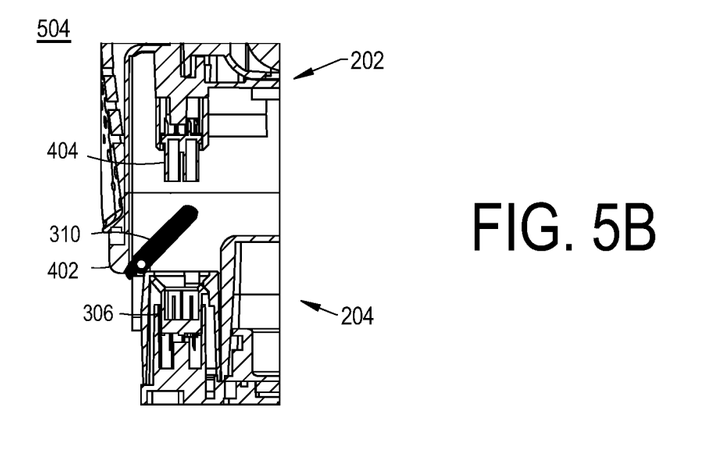
FIG. 5B is a sectional view illustrating the PAP device of FIG. 5A in a second position, according to example embodiments.
Figure 5C:
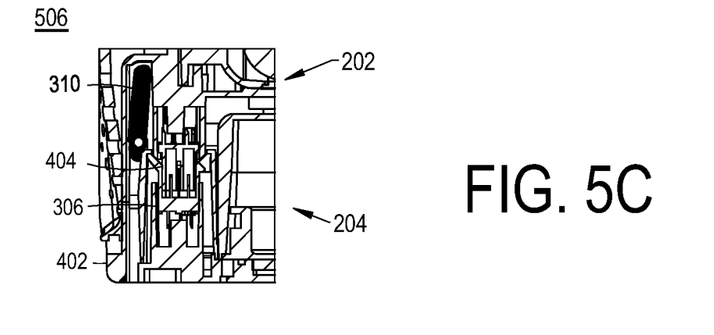
FIG. 5C is a sectional view illustrating the PAP device of FIG. 5A in a third position, according to example embodiments.

FIG. 5A is a sectional view illustrating PAP device 100 in a first position 502, according to example embodiments. FIG. 5B is a sectional view illustrating PAP device 100 in a second position 504, according to example embodiments. FIG. 5C is a sectional view illustrating PAP device 100 in a third position 506, according to example embodiments. For ease of discussion, FIGS. 5A, 5B, and 5C may be discussed and described together.

As shown across FIGS. 5A-5C, primary housing 202 may be lowered onto humidification system 204. In FIG. 5A, primary housing 202 is in first position 502 relative to humidification system 204. In first position 502, primary housing 202 may be completely detached from humidification system 204. In such embodiments, lid 310 is completely covering electronic connector interface 306.

In FIG. 5B, primary housing 202 is in second position 504 relative to humidification system 204. In second position 504, edge wall 402 of primary housing 202 may physically contact lid 310. Such physical contact may begin to force lid 310 into an open position, thus partially exposing electronic connector interface 306.

In FIG. 5C, primary housing 202 is in third position 506 relative to humidification system 204. In third position 506, primary housing 202 may be coupled with humidification system 204, such as that described and shown above in conjunction with FIG. 2C. When primary housing 202 is coupled with humidification system 204, edge wall 402 may have forced lid 310 into a completely open position. In the completely open position, male electronic connection interface 404 of primary housing 202 may mate with electronic connector interface 306. Such electrical connection is what ultimately provides power to heating plate 312.

Figure 6A:
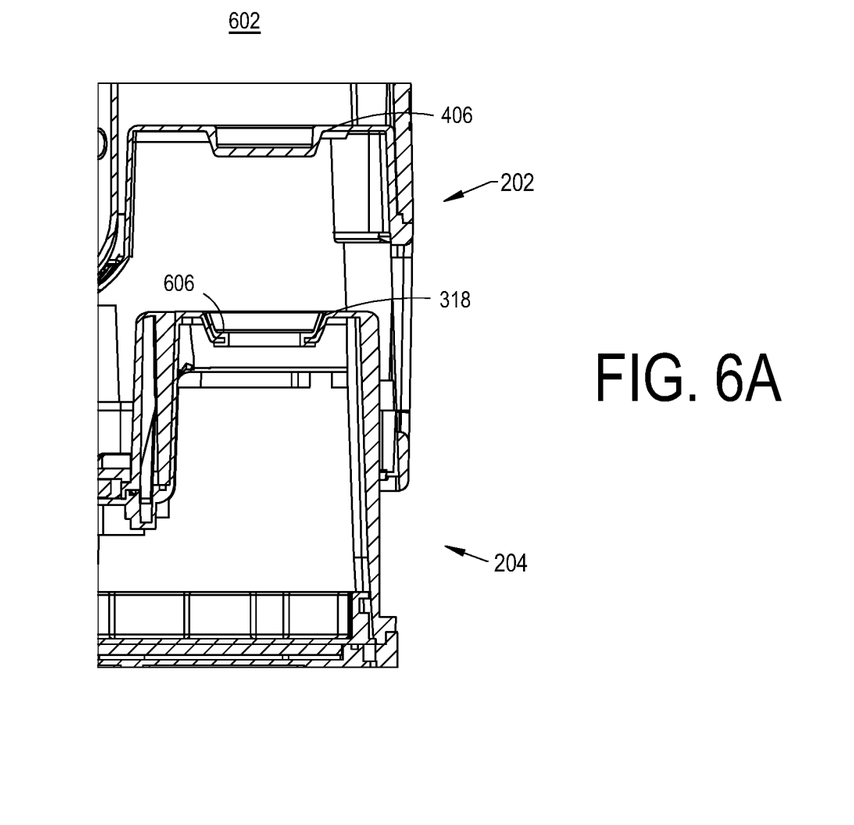
FIG. 6A is a sectional view illustrating a PAP device in a first position, according to example embodiments.
Figure 6B:
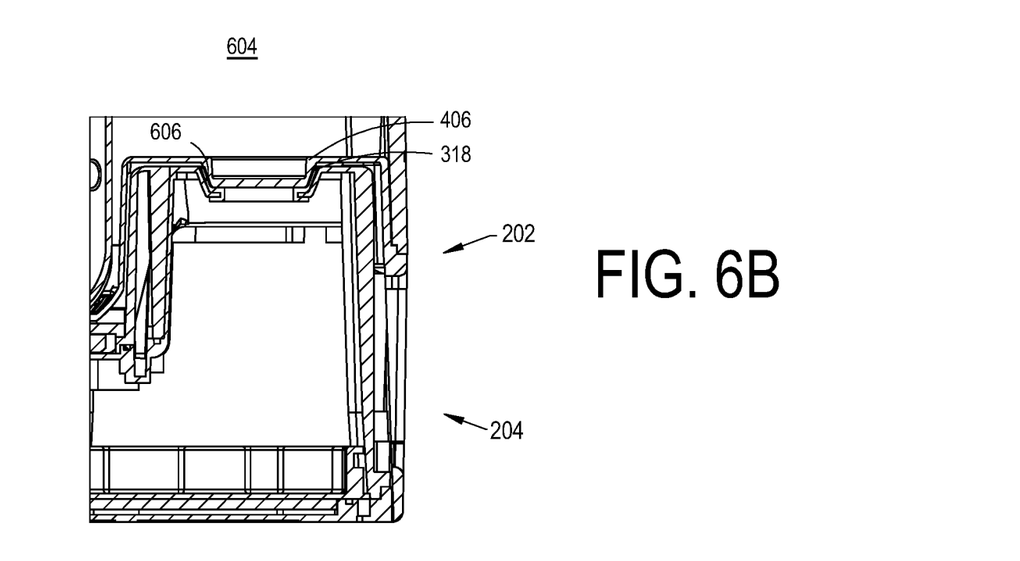
FIG. 6B is a sectional view illustrating the PAP device of FIG. 6A in a second position, according to example embodiments.

FIG. 6A is a sectional view illustrating PAP device 100 in a first position 602, according to example embodiments. FIG. 6B is a sectional view illustrating PAP device 100 in a second position 604, according to example embodiments. For ease of discussion, FIGS. 6A-6B may be discussed and described together.

As shown across FIGS. 6A-6B, primary housing 202 may be lowered onto humidification system 204. In FIG. 6A, primary housing 202 is in first position 602 relative to humidification system 204. In first position, primary housing 202 is hovering partially over second position 604, but is not completely detached from humidification system 204. In first position 602, pour hole interface 210 may be at least partially exposed.

In FIG. 6B, primary housing 202 is in second position 604 relative to humidification system 204. In second position 604, primary housing 202 may be coupled with humidification system 204, such as that described and shown above in conjunction with FIG. 2C and FIG. 5C. When primary housing 202 is coupled with humidification system 204, conical hub 406 may automatically seal pour hole interface 210 through compression. For example, conical hub 406 may automatically sear pour hole interface 210 by providing compression against pour hole seal 606 of pour hole interface 210. In some embodiments, pour hole seal 606 may be formed from silicone, silicone rubber, or any other appropriate material that is rigid enough to remain fixed in place while also having a soft enough durometer so that conical hub 406 can efficiently seal pour hole seal 606 when primary housing 202 and humidification system 204 are fully connected.

Figure 7:
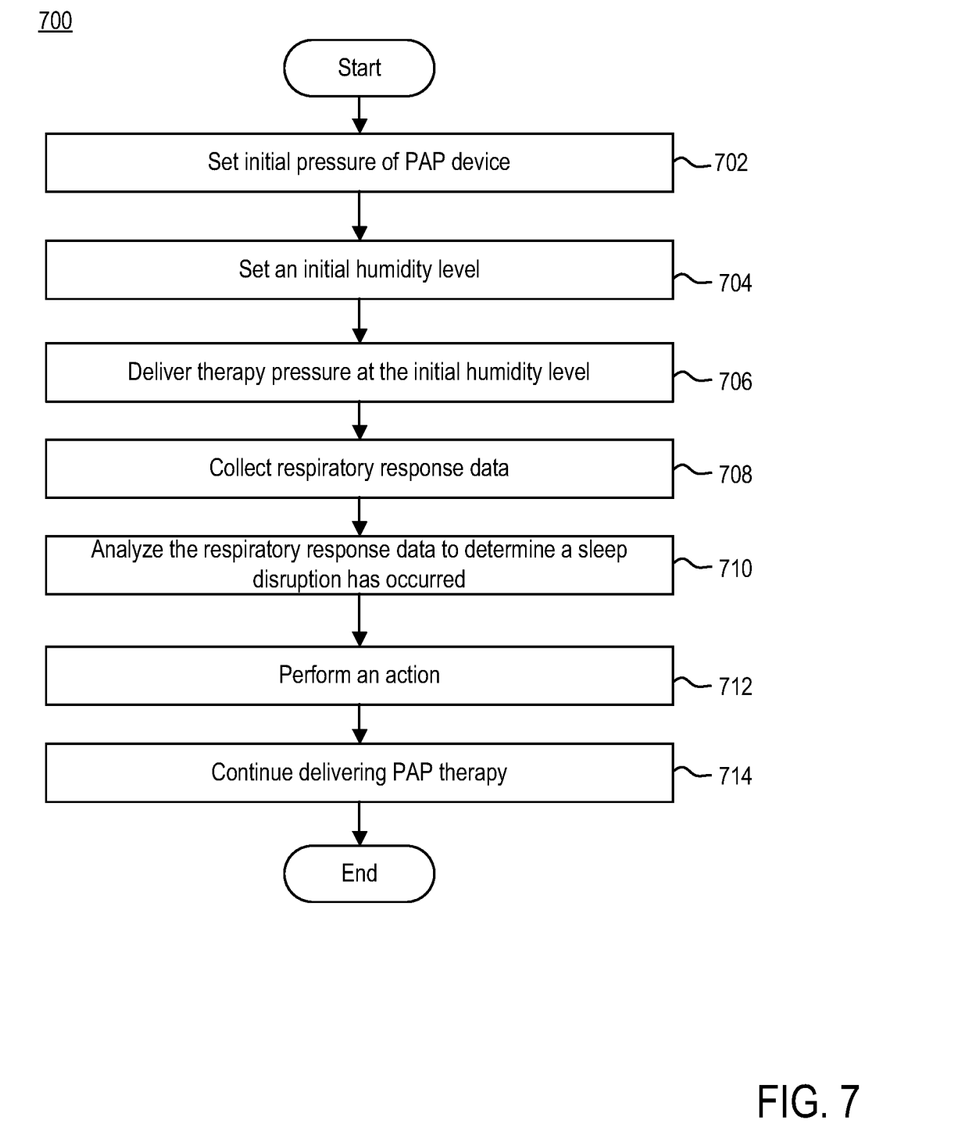
FIG. 7 is a flow diagram illustrating a method of administrating PAP therapy, according to example embodiments.

FIG. 7 is a flow diagram illustrating a method 700 of administrating PAP therapy, according to example embodiments. Method 700 may begin at step 702.

At step 702, microprocessor 114 may set the initial therapy pressure of PAP device 100. For example, microprocessor 114 may send a control signal to blower controller 116 that instructs blower controller 116 to set a speed of blower 106 to achieve the initial therapy pressure delivered to patient 101.

At step 704, microprocessor 114 may set an initial humidity levels of PAP device 100. For example, microprocessor 114 may send a control signal to electronic connector interface 306 that instructs electronic connector interface 306 to supply power to heating plate 312 to achieve the initial humidity level of the initial therapy pressure delivered to patient 101.

In some embodiments, microprocessor 114 may set the initial humidity level of PAP device 100 to a default initial humidity level. In some embodiments, microprocessor 114 may set the initial humidity level of PAP device 100 based on input instructions from patient 101 or someone associated with patient 101 (e.g., clinician, family member, etc.). In some embodiments, the input instructions may be received through selection device 216 and/or display 218.

At step 706, PAP device 100 may deliver the therapy pressure at the initial humidity level to patient 101. For example, blower 106 may be set at a speed, such that the therapy pressure is achieved; heating plate 312 may be set to a temperature so that the initial humidity level is achieved.

PAP device 100 may deliver the set pressure to patient 101 via patient delivery system 124.

At step 708, microprocessor 114 may collect respiratory response data based on the set pressure delivered to patient 101. For example, during delivery of set pressure, sensor 130 may record pressure readings. and sensor 132 may record temperature readings.

At step 710, microprocessor 114 may analyze the respiratory response data to determine whether a sleep disruption has occurred. In some embodiments, analyzing the respiratory response may include sleep disruption module comparing the collected respiratory response data to the patient's baseline respiratory response data.

At step 712, microprocessor 114 may perform some action. In some embodiments, the action may be to send a control signal to blower controller 116 that causes blower controller 116 to change the speed of blower 106, thereby adjusting the therapy pressure delivered to patient 101. In some embodiments, the action may be to send a control signal to electronic connector interface 306 to change the temperature of heating plate 312, thereby adjusting the humidity of the therapy pressure delivered to patient 101. In some embodiments, the action may be to issue an alert to a clinician.

At step 714, microprocessor 114 may continue delivering PAP therapy to patient 101.

Figure 8A:
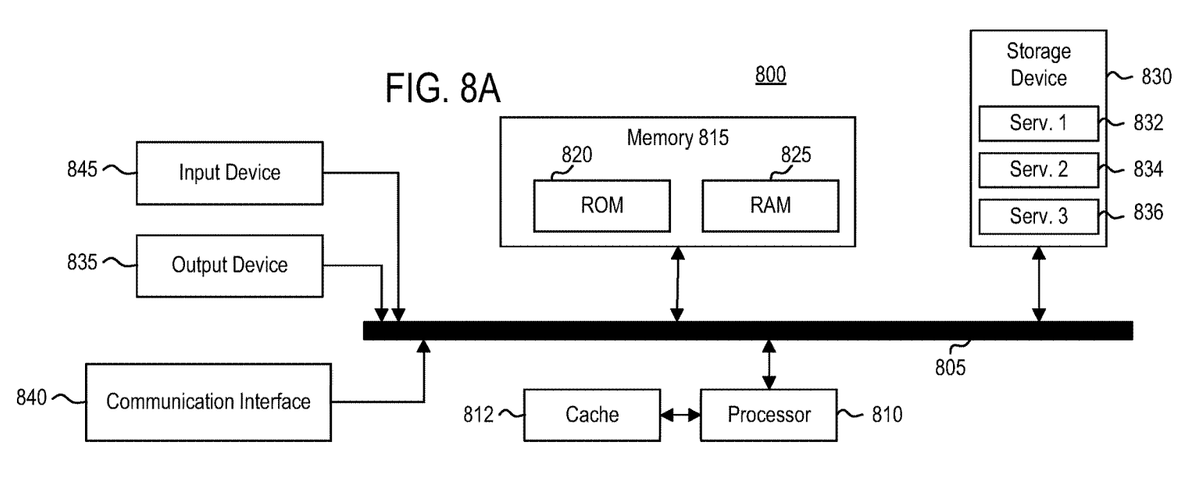
FIG. 8A is a block diagram illustrating a computing device, according to example embodiments.

FIG. 8A illustrates a system bus architecture of computing system 800, according to example embodiments. System 800 may be representative of at least a portion of microprocessor 114 and/or blower controller 116. One or more components of system 800 may be in electrical communication with each other using a bus 805. System 800 may include a processing unit (CPU or processor) 810 and a system bus 805 that couples various system components including the system memory 815, such as read only memory (ROM) 820 and random access memory (RAM) 825, to processor 810. System 800 may include a cache of high-speed memory connected directly with, in close proximity to, or integrated as part of processor 810. System 800 may copy data from memory 815 and/or storage device 830 to cache 812 for quick access by processor 810. In this way, cache 812 may provide a performance boost that avoids processor 810 delays while waiting for data. These and other modules may control or be configured to control processor 810 to perform various actions. Other system memory 815 may be available for use as well. Memory 815 may include multiple different types of memory with different performance characteristics. Processor 810 may include any general purpose processor and a hardware module or software module, such as service 1 832, service 2 834, and service 3 836 stored in storage device 830, configured to control processor 810 as well as a special-purpose processor where software instructions are incorporated into the actual processor design. Processor 810 may essentially be a completely self-contained computing system, containing multiple cores or processors, a bus, memory controller, cache, etc. A multi-core processor may be symmetric or asymmetric.

To enable user interaction with the computing system 800, an input device 845 may represent any number of input mechanisms, such as a microphone for speech, a touch-sensitive screen for gesture or graphical input, keyboard, mouse, motion input, speech and so forth. An output device 835 may also be one or more of a number of output mechanisms known to those of skill in the art. In some instances, multimodal systems may enable a user to provide multiple types of input to communicate with computing system 800. Communications interface 840 may generally govern and manage the user input and system output. There is no restriction on operating on any particular hardware arrangement and therefore the basic features here may easily be substituted for improved hardware or firmware arrangements as they are developed.

Storage device 830 may be a non-volatile memory and may be a hard disk or other types of computer readable media which may store data that are accessible by a computer, such as magnetic cassettes, flash memory cards, solid state memory devices, digital versatile disks, cartridges, random access memories (RAMs) 825, read only memory (ROM) 820, and hybrids thereof.

Storage device 830 may include services 832, 834, and 836 for controlling the processor 810. Other hardware or software modules are contemplated. Storage device 830 may be connected to system bus 805. In one aspect, a hardware module that performs a particular function may include the software component stored in a computer-readable medium in connection with the necessary hardware components, such as processor 810, bus 805, output device 835 (e.g., display), and so forth, to carry out the function.

Figure 8B:
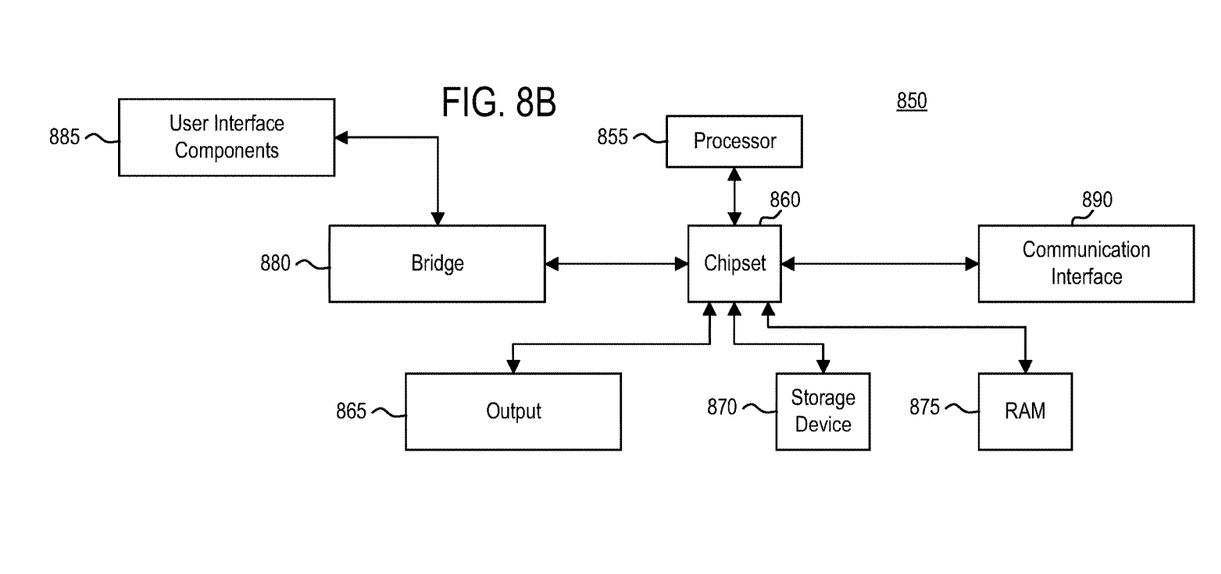
FIG. 8B is a block diagram illustrating a computing device, according to example embodiments.

FIG. 8B illustrates a computer system 850 having a chipset architecture that may represent at least a portion of microprocessor 114 and/or blower controller 116. Computer system 850 may be an example of computer hardware, software, and firmware that may be used to implement the disclosed technology. System 850 may include a processor 855, representative of any number of physically and/or logically distinct resources capable of executing software, firmware, and hardware configured to perform identified computations. Processor 855 may communicate with a chipset 860 that may control input to and output from processor 855. In this example, chipset 860 outputs information to output 865, such as a display, and may read and write information to storage device 870, which may include magnetic media, and solid state media, for example. Chipset 860 may also read data from and write data to storage device 875 (e.g., RAM). A bridge 880 for interfacing with a variety of user interface components 885 may be provided for interfacing with chipset 860. Such user interface components 885 may include a keyboard, a microphone, touch detection and processing circuitry, a pointing device, such as a mouse, and so on. In general, inputs to system 850 may come from any of a variety of sources, machine generated and/or human generated.

Chipset 860 may also interface with one or more communication interfaces 890 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 855 analyzing data stored in storage device 870 or storage device 875. Further, the machine may receive inputs from a user through user interface components 885 and execute appropriate functions, such as browsing functions by interpreting these inputs using processor 855.

It may be appreciated that example systems 800 and 850 may have more than one processor 810 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

The invention claimed is:

1. A positive airway pressure device, comprising:
 a primary housing comprising:
  an outer edge,
  a first electronic connection portion,
  a blower configured to deliver a vapor to a patient, and
  a chamber; and
 a humidification system comprising:
  a water reservoir configured to hold a liquid,
  a heating plate in thermal communication with the water reservoir,
  a second electronic connection portion, and
  a lid configured to selectively shield the second electronic connection portion,
 the primary housing configurable between at least two positions relative to the humidification system, the at least two positions comprising a first position in which the lid at least partially shields the second electronic connection portion and a second position in which the outer edge of the primary housing forces open the lid such that the first electronic connection portion mates with the second electronic connection portion, and
 wherein, in the second position, the chamber is configured to receive vapor generated by the blower and the heating plate and output the vapor to the patient.

2. The positive airway pressure device of claim 1, wherein the primary housing further comprises:
 a first sensor at least partially disposed in a gas pathway, the first sensor configured to measure a pressure in the chamber; and
 a second sensor at least partially disposed in the gas pathway, the second sensor configured to measure a temperature in the chamber.

3. The positive airway pressure device of claim 1, further comprising:
 a controller in communication with the blower and at least one of the first electronic connection portion or the second electronic connection portion.

4. The positive airway pressure device of claim 1, wherein the humidification system comprises:
 a heater module; and
 a water chamber module, wherein the heater module is configured to heat the liquid contained in the water chamber module.

5. The positive airway pressure device of claim 4, wherein the heater module and the water chamber module are configured between at least a third position and a fourth position, wherein, in the third position, the heater module is separate and detached from the water chamber module and, wherein, in the fourth position, the heater module is interfaced with the water chamber module.

6. The positive airway pressure device of claim 1, further comprising:
 an ultraviolet light configured to sterilize the liquid in the humidification system.

7. The positive airway pressure device of claim 1, further comprising:
 a valve configurable between an open position and a closed position, the valve configured to prevent asphyxiation during therapy.

8. The positive airway pressure device of claim 7, wherein the humidification system comprises:
 a heater module; and
 a water chamber module, wherein the heater module is configured to heat the liquid contained in the water chamber module.

9. A positive airway pressure device, comprising:
 a primary housing comprising:
  an outer edge,
  a first electronic connection portion, and
  a blower configured to deliver a vapor to a patient; and
 a humidification system comprising:
  a water reservoir configured to hold a liquid,
  a heating plate in thermal communication with the water reservoir,
  a second electronic connection portion, and
  a lid configured to selectively shield the second electronic connection portion,
 wherein the lid is a spring-loaded lid that is lifted when the primary housing is coupled and engaged with the humidification system,
 the primary housing configurable between at least two positions relative to the humidification system, the at least two positions comprising a first position in which the lid at least partially shields the second electronic connection portion and a second position in which the outer edge of the primary housing forces open the lid such that the first electronic connection portion mates with the second electronic connection portion.

10. A positive airway pressure device, comprising:
 a primary housing comprising:
  an outer edge,
  a first electronic connection portion,
  a blower configured to deliver a vapor to a patient, and
  a conical hub; and
 a humidification system comprising:
  a water reservoir configured to hold a liquid,
  a heating plate in thermal communication with the water reservoir,
  a second electronic connection portion,
  a lid configured to selectively shield the second electronic connection portion, and a pour hole interface in communication with the water reservoir, the primary housing configurable between at least two positions relative to the humidification system, the at least two positions comprising a first position in which the lid at least partially shields the second electronic connection portion and a second position in which the outer edge of the primary housing forces open the lid such that the first electronic connection portion mates with the second electronic connection portion.

11. The positive airway pressure device of claim 10, wherein, in the first position, the conical hub is not interfaced with the pour hole interface and, wherein, in the second position, the conical hub is interfaced with the pour hole interface.

12. A positive airway pressure device, comprising:
a primary housing comprising:
    a first electronic connection portion,
    a chamber,
    a first sensor at least partially disposed in a gas pathway, the first sensor configured to measure a pressure in the chamber,
    a second sensor at least partially disposed in the gas pathway, the second sensor configured to measure a temperature in the chamber, and
    a blower configured to deliver a vapor to a patient;
a humidification system comprising:
    a water reservoir configured to hold a liquid,
    a heating plate in thermal communication with the water reservoir, and
    a second electronic connection portion configured to interface with the first electronic connection portion,
    wherein the chamber is configured to receive vapor generated by the blower and the heating plate and output the vapor to the patient; and
a controller in communication with the blower and at least one of the first electronic connection portion or the second electronic connection portion.

13. The positive airway pressure device of claim 12, wherein the controller is configured to adjust the temperature of the heating plate based on temperature readings measured by the second sensor.

14. The positive airway pressure device of claim 12, further comprising:
a valve configurable between an open position and a closed position, the valve configured to prevent asphyxiation during therapy.

* * * * *